United States Patent [19]
Kadowaki et al.

[11] Patent Number: 5,351,282
[45] Date of Patent: Sep. 27, 1994

[54] MOBILE X-RAY APPARATUS

[75] Inventors: Toshio Kadowaki, Kyoto; Shojiro Yamaguchi, Uji, both of Japan

[73] Assignee: Shimadzu Corporation, Kyoto, Japan

[21] Appl. No.: 36,275

[22] Filed: Mar. 24, 1993

[30] Foreign Application Priority Data

Mar. 31, 1992 [JP] Japan .................................. 4-109028
Jun. 29, 1992 [JP] Japan .............................. 4-51784[U]

[51] Int. Cl.$^5$ .............................................. H05G 1/02
[52] U.S. Cl. .................................... 378/198; 378/193; 378/197
[58] Field of Search ............... 378/198, 193, 197, 196, 378/204; 180/6.2, 6.48, 6.5, 19.1, 19.2, 19.3

[56] References Cited

U.S. PATENT DOCUMENTS

| | | | |
|---|---|---|---|
| 4,341,279 | 7/1982 | Waerve | 180/19.2 |
| 4,646,862 | 3/1987 | Meili | 180/19.3 |
| 4,697,661 | 10/1987 | Pajerski et al. | 180/6.5 |
| 4,709,771 | 12/1987 | Basham et al. | 180/19.3 X |
| 4,829,844 | 5/1989 | Boomgaarden et al. | 180/6.5 X |
| 5,064,010 | 11/1991 | Masbruch et al. | 180/19.3 X |

*Primary Examiner*—David P. Porta
*Attorney, Agent, or Firm*—Nikaido, Marmelstein, Murray & Oram

[57] ABSTRACT

A mobile X-ray apparatus having a carriage driven in a direction in which forces are applied to a pair of right and left control bars operable without influencing each other. The right and left control bars are arranged symmetrically with respect to the direction of movement of the carriage. Each control bar is supported to be pivotable independently of the other in a substantially horizontal or vertical plane. A neutralizing mechanism is provided for maintaining each control bar in a neutral position when the control bar is free from an external force. Position detectors are disposed adjacent a forward position and a rearward position of each control bar, respectively, to detect displacement thereof. Each control bar has an equivalent capacitor structure having an electrostatic capacity variable when the operator grips the control bar. This structure provides a safety mechanism for allowing the carriage to move only when the operator grips the control bar.

8 Claims, 6 Drawing Sheets

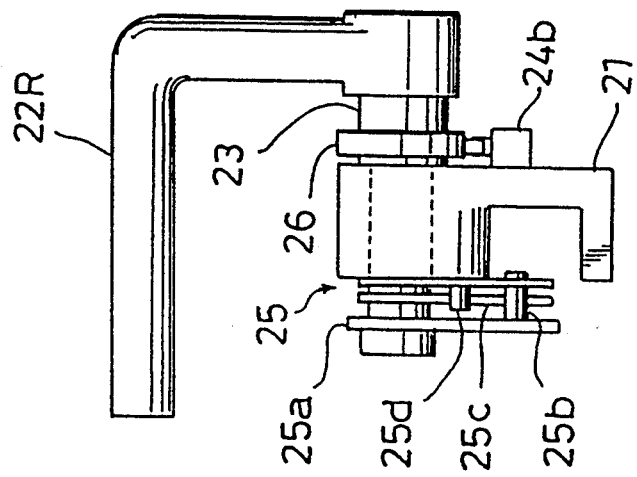
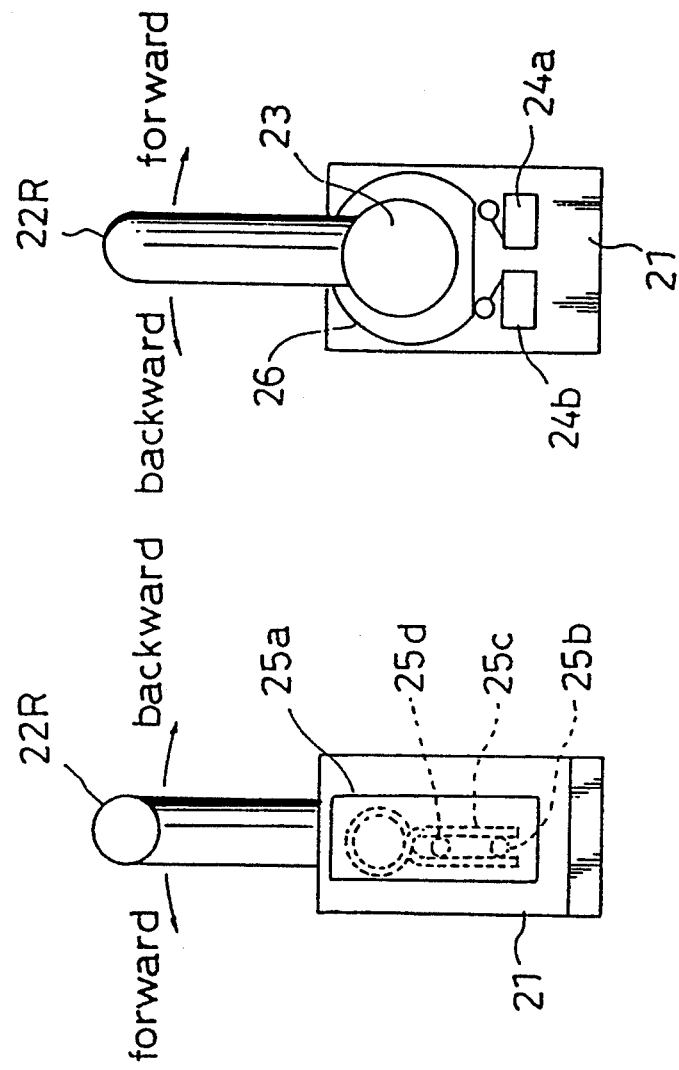

MOBILE X-RAY APPARATUS

BACKGROUND OF THE INVENTION

1. Field of the Invention

The present invention relates to mobile X-ray apparatus used in taking X-ray photographs of immovable patients in operating rooms or emergency treatment rooms of medical institutions, or in taking X-ray photographs on rounds, and more particularly to a steering mechanism for this type of apparatus.

2. Description of the Related Art

Conventionally, this type of apparatus has an X-ray tube, an X-ray tube control unit, a carriage driving control unit and so forth mounted on a power-driven carriage. An operator standing behind the carriage manipulates a steering control bar or bars to drive the carriage.

In one example of mechanisms for steering the carriage, a control bar secured to a main body of the apparatus has a portion thereof rotatable about its axis in the same way as the accelerator of a motorcycle is rotated. A direction of rotation is detected for driving the carriage forward or backward. An angle of rotation of the control bar is also detected and outputted as a moving speed signal to the driving control unit.

In another example, as disclosed in U.S. Pat. No. 4,697,661, a single control bar is supported by a main body of an apparatus such that opposite ends of the bar are displaceable. When an operator applies forces to the control bar, displacements of the opposite ends of the bar are detected. Respective displacement signals are outputted to a control unit as steering signals for controlling a pair of drive wheels of a carriage.

The conventional apparatus noted above have the following disadvantages:

The former provides an unnatural feeling of control since the rotation of the control bar is unlike the feeling of "push forward" or "pull backward". Besides, it is not simple or easy to provide the same control bar with means for outputting turnabout signals.

In the latter, the operator normally holds the opposite ends of the control bar with both hands to control the carriage. Since only one bar is provided, right and left operating forces and amounts of displacement influence one another to provide an unnatural feeling of control. When the operator pushes only the left end of the control bar, for example, the right end of the control bar will also be displaced slightly. As a result, not only the left drive wheel but the right drive wheel will also make a slight movement. Thus, an actual movement of the carriage deviates from the feeling of control.

SUMMARY OF THE INVENTION

The present invention has been made having regard to the state of the art noted above. A primary object of the invention, therefore, is to provide a mobile X-ray apparatus with a steering mechanism having a relatively simple construction, in which directions of forces applied to right and left control bars agree with an intended direction of movement of the apparatus, while each of the control bars is free from influences of the other.

Another object of the present invention is to provide a mobile X-ray apparatus with a safety mechanism having an excellent operability for preventing a carriage from moving inadvertently when an operator unintentionally touches a control bar.

The above objects are fulfilled, according to the present invention, by a mobile X-ray apparatus having a power-driven carriage with a pair of drive wheels and at least one swivelable auxiliary wheel, an X-ray tube movably supported on the carriage, and an X-ray tube control unit and a carriage drive unit mounted on the carriage, the apparatus comprising a pair of control bars arranged opposite each other in a control section provided on the carriage, each of the control bars being supported to be independently pivotable about an axis and displaceable substantially in a direction of movement of the carriage; a neutralizing mechanism for maintaining each of the control bars in a neutral position when the control bar is free from an external force; position detecting means for detecting displacements of the control bars in directions to drive the carriage forward and backward, respectively; and drive means responsive to detection signals received from the position detecting means for controlling opposite rotations of each of the drive wheels.

According to the present invention, when the operator displaces the control bars in a direction in which he or she intends to move the carriage, the position detecting means detects the displacements of the control bars and output respective detection signals to the drive means. Based on the detection signals, the drive means rotates the respective drive wheels in the intended direction. For example, the carriage moves forward when the pair of control bars are both displaced in a direction to drive the carriage forward. The carriage moves backward when the pair of control bars are both displaced in a direction to drive the carriage backward. The carriage makes a turn while moving forward (or backward) when one of the control bars is displaced forward (or backward) with the other maintained in the neutral position. The carriage turns round without moving forward or backward when the control bars are displaced in opposite directions.

The present invention provides a natural feeling of control since the moving directions of the carriage correspond to the directions of displacement of the control bars as noted above. Further, since the control bars are independent of each other, the movement of one control bar imparts no influence on the other. Thus, the carriage may be driven easily with a natural feeling of control.

Each of the control bars is pivotable in a horizontal plane, and is disposed such that an axis thereof lies on a line extending substantially perpendicular to a direction of movement of the carriage. Alternatively, each of the control bars comprises an L-shaped bar having a proximal portion thereof supported to be pivotable in a vertical plane, a distal portion of each control bar being disposed such that an axis thereof lies on a line extending substantially perpendicular to a direction of movement of the carriage.

Various sensors may be used as the position detecting means for detecting the displacements of the control bars, such as microswitches, photoelectric switches or proximity switches.

According to the present invention, the carriage stands still with the control bars placed in the neutral positions when no external forces are applied to the control bars. The neutralizing mechanism includes, for example, a pair of levers each pivotably supported at one end thereof, the other ends of the levers being interconnected through a coil spring. Each of the control bars is held between the levers to be maintained in the neutral position. In another example, the neutralizing mechanism includes a torsion spring mounted on a pivotal axis connected to one of the control bars, the spring being engaged at one end thereof with a free end of an arm connected to the pivotal axis, and at the other end with a bracket of the pivotal axis, to maintain the control bar in the neutral position.

Further, the present invention provides a safety mechanism including grip detecting means for detecting grips by an operator of the pair of control bars. The drive means validates the detection signals received from the position detecting means only when the grip detecting means outputs a detection signal.

This safety mechanism assures safety in that the carriage will not move inadvertently when the operator touches the control bars through carelessness, The grip detecting means may be in the form of a lever, similar to a brake lever of a motorcycle, provided alongside each control bar, so that the carriage is movable only when the lever and control bar are gripped together. However, this construction would give an unnatural feeling to the operator, and its operability would be unsatisfactory.

The following example may be given as a safety mechanism having excellent operability:

Each of the control bars has an equivalent capacitor structure including a core formed of a conductive material, an insulating coating formed around the core, and a conductive element extending axially of the control bar and exposed from a periphery of the insulating coating facing the direction to drive the carriage forward. The grip detecting means is operable to detect variations in electrostatic capacity of the control bars occurring when the operator grips the control bars.

The control bars are disposed rearwardly of the carriage. The conductive elements exposed in the direction to drive the carriage forward are concealed from the operator who stands behind the control bars. Thus, the conductive elements are not touched by the operator's hands unless he or she grips the control bars.

BRIEF DESCRIPTION OF THE DRAWINGS

For the purpose of illustrating the invention, there are shown in the drawings several forms which are presently preferred, it being understood, however, that the invention is not limited to the precise arrangements and instrumentalities shown.

FIG. 7 is an enlarged view of a principal portion of the second embodiment,

FIG. 8 is a right side view of the portion shown in FIG. 7,

FIG. 9 is a left side view of the portion shown in FIG. 7,

DESCRIPTION OF THE PREFERRED EMBODIMENTS

Preferred embodiments of the present invention will be described in detail hereinafter with reference to the drawings.

FIRST EMBODIMENT

Figure 1:
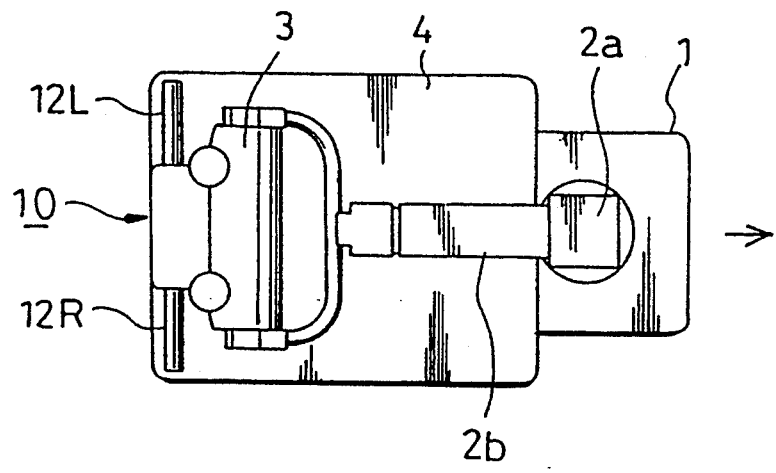
FIG. 1 is a schematic plan view of a first embodiment.
Figure 2:
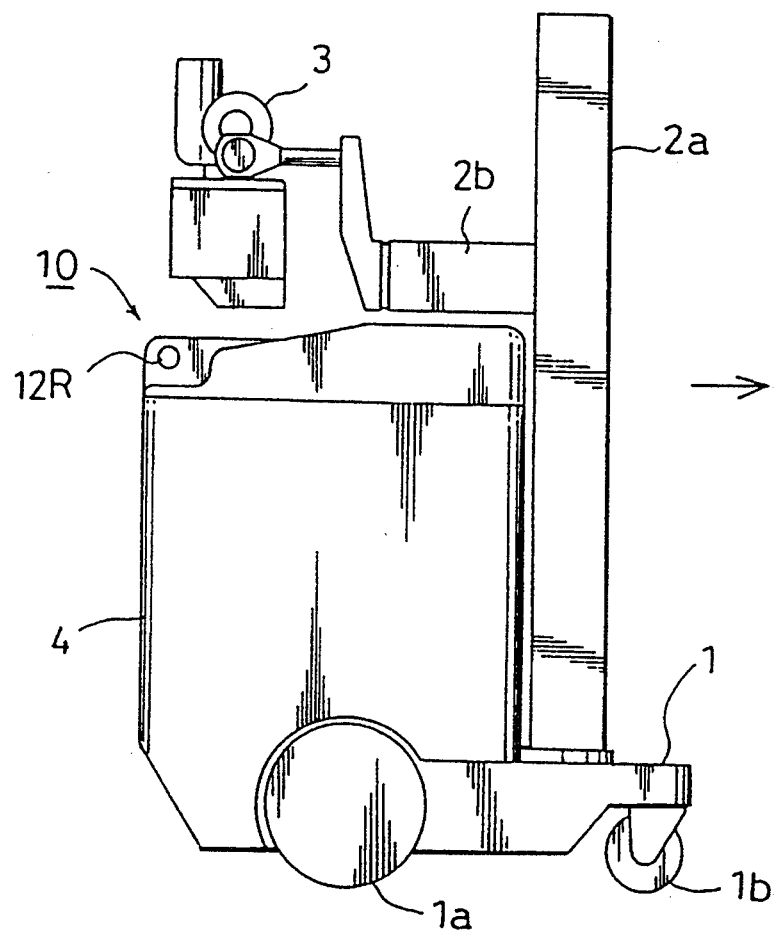
FIG. 2 is a schematic front view of the first embodiment.

As shown in FIGS. 1 and 2, a mobile X-ray apparatus 10 according to the present invention includes a power-driven carriage 1 having a pair of drive wheels (rear wheels) 1a and one caster (front wheel) (or a pair of casters) 1b. A column 2a is erected on the carriage 1 and has a support arm 2b attached thereto to be vertically slidable and pivotable in a horizontal plane. The support arm 2b supports an X-ray tube 3 attached to a distal end thereof to be pivotable in a vertical plane. The carriage 1 further supports a control box 4 containing an X-ray control unit for controlling the X-ray tube 3 and a carriage drive unit for driving the carriage 1. A control section provided above the control box 4 includes a pair of left and right control bars 12L and 12R. Each of the control bars 12L and 12R is pivotable in a horizontal plane independently of the other to be displaced substantially in a direction of movement of the carriage 1. Each control bar 12L or 12R is disposed such that an axis thereof lies on a line extending substantially perpendicular to the direction of movement of the carriage 1.

Figure 3:
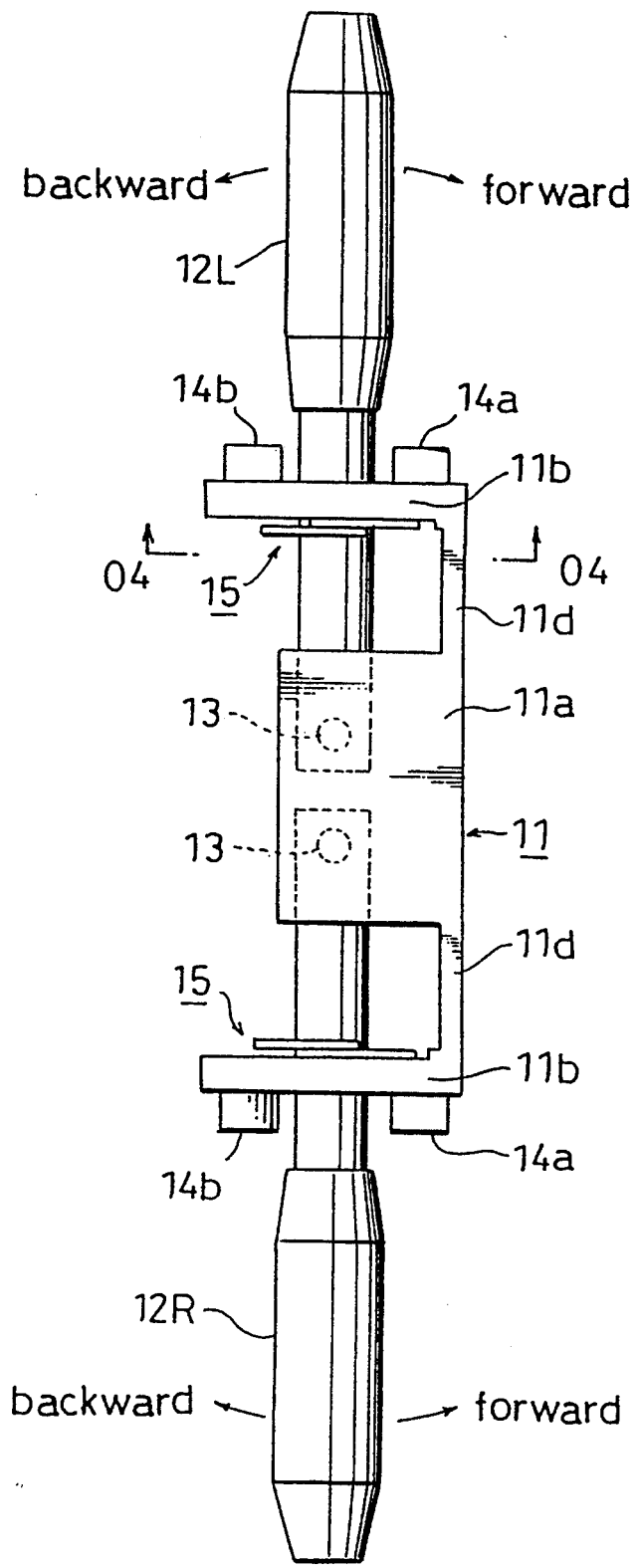
FIG. 3 is an enlarged view of a principal portion of the first embodiment.
Figure 4:
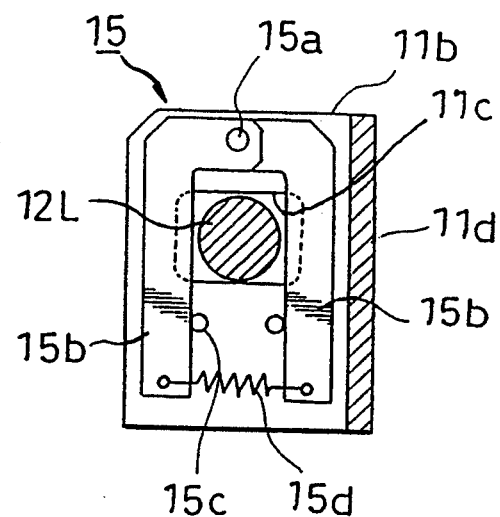
FIG. 4 is a section taken on line 04—04 of FIG. 3.
Figure 6:
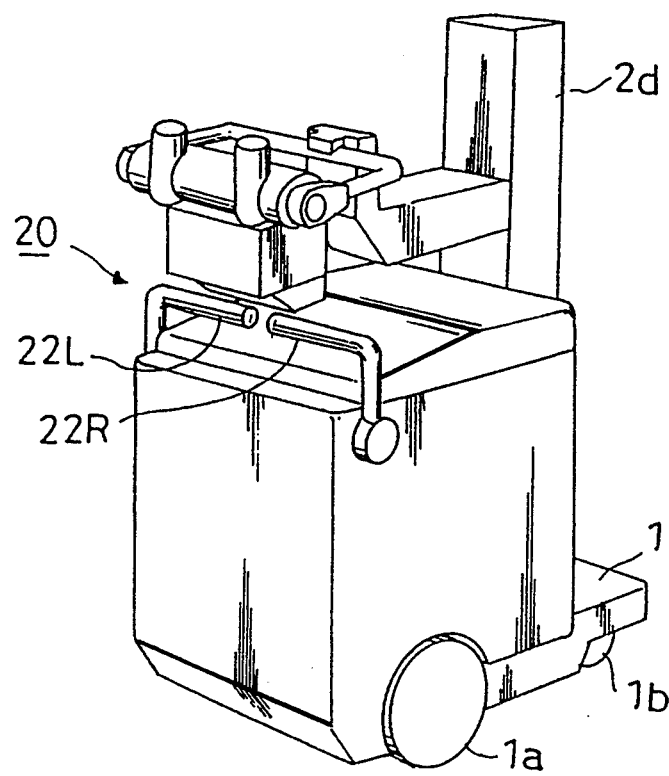
FIG. 6 is a schematic perspective view of a second embodiment.

A structure for supporting the control bars 12L and 12R will particularly be described with reference to FIGS. 3 and 4. The control section of the carriage 1 has a support frame 11 for supporting the left and right control bars 12L and 12R arranged symmetrically. The support frame 11 includes a central portion 11a in the form of a rectangular parallelopiped to which end portions 11b are connected through connecting portions 11d. Each of the end portions 11b defines an elliptical guide bore 11c slightly elongated in the fore and aft direction. The control bars 12L and 12R are supported by the central portion 11a through pivotal axes 13 to be pivotable substantially in a horizontal plane, respectively.

A neutralizing mechanism 15 including a spring is provided to place the axis of each control bar 12L or 12R in a direction extending left or right (i.e. in a neutral position) when the carriage 1 stands still, while allowing the axis to tilt forward when the carriage 1 moves forward, and backward when the carriage 1 moves backward. Specifically, each end portion 11b has a pivotal axis 15a projecting transversely inwardly therefrom for supporting two L-shaped levers 15b to be pivotable in fore and aft directions. Further, each end portion 11b has two pins 15c projecting transversely inwardly therefrom for positioning lower parts of the levers 15b. A tension spring 15b extends between lower positions of the two levers 15b.

Each end portion 11b has microswitches 14a and 14b mounted on an outer lateral wall thereof adjacent forward and backward positions of the control bar 12L or 12R to act as forward and backward position detecting means, respectively.

Figure 5:
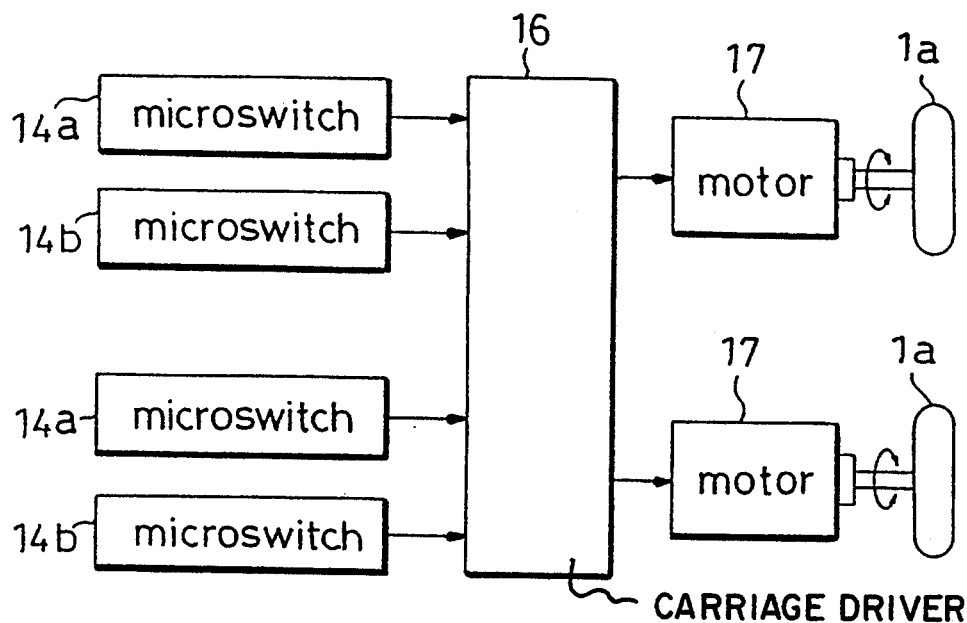
FIG. 5 is a block diagram of a control system of the first embodiment.

The mobile X-ray apparatus 10 having the above construction is moved by an operator gripping the left and right control bars 12L and 12R. As shown in FIG. 5, each of the left and right drive wheels 1a receives torque from an associated motor 17. When the control bars 12L and 12R are pushed forward or pulled backward, their displacements are detected by the microswitches 14a or 14b which transmit corresponding signals to a carriage drive unit 16. The drive unit 16 determines rotating directions of the left and right drive wheels 1a based on a combination of directions of displacement of the left and right control bars 12L and 12R. The following table shows combinations of directions of displacement of the left and right control bars 12L and 12R, rotations corresponding thereto of the left and right drive wheels 1a, and directions of movement of the apparatus. As seen from the table, the apparatus is freely movable forward or backward or capable of turning round by pushing or pulling the control bars 12L and 12R.

TABLE

| left bar | right bar | left wheel | right wheel | apparatus movement |
| --- | --- | --- | --- | --- |
| — | — | — | — | still |
| push | push | forward | forward | straight forward |
| push | — | forward | — | forward & turn right |
| push | pull | forward | backward | turn round right |
| — | push | — | forward | forward & turn left |
| pull | push | backward | forward | turn round left |
| pull | pull | backward | backward | straight backward |
| pull | — | backward | — | backward & turn right |
| — | pull | — | backward | backward & turn left |

SECOND EMBODIMENT

A second embodiment will be described next with reference to FIGS. 6 through 9. A mobile X-ray apparatus 20 in this embodiment includes L-shaped left and right control bars 22L and 22R having proximal portions thereof pivotable in substantially vertical planes. Specifically, a bracket-like support frame 21 rotatably supports a horizontal pivotal axis 23, and each of the control bars 22L and 22R extends upward from an end of the axis 23.

A neutralizing mechanism 25 includes an arm 25a projecting downward from the other end of the pivotal axis 23, a first pin 25b projecting from the arm 25a toward the support frame 21, a second pin 25d projecting from the support frame 21, and a torsion spring 25c fitted on the pivotal axis 23 adjacent the other end. The spring 25c is engaged at opposite ends thereof with the two pins 25b and 25d. Numerals 24a and 24b denote microswitches acting as forward and backward position detecting means.

THIRD EMBODIMENT

With the apparatus in the first and second embodiments described above, the carriage could move inadvertently when the operator touches the control bars through carelessness. A mobile X-ray apparatus in this embodiment has a safety mechanism to avoid such an incident.

The safety mechanism characterizing this embodiment will be described hereinafter with reference to FIGS. 10 through 13. The carriage and the components such as the X-ray tube mounted thereon are the same as in the first and second embodiments, and will not be described again.

Each control bar 30 has a substantially cylindrical shape, and includes a core 31 formed of a conductive material such as steel, and a coating 32 formed of an insulating material such as urethane and surrounding the core 31. An electrode 33 formed of a conductor such as aluminum is embedded in the coating 32 to be out of contact with the core 31 and extending axially thereof. The electrode 33 is partly exposed from a surface of the coating 32 facing a forward direction of the carriage (i.e. a surface facing away from the standing operator).

A sensor mechanism for detecting a grip of the operator (FIG. 11) and a drive detecting circuit using the sensor will be described next with reference to FIGS. 10 through 13.

Though not shown, a sensor 41 includes a high frequency oscillator, a current detector, and a mechanism for comparing a detected current with a predetermined threshold level and outputting information on a result of comparison in binary form (e.g. "ON" and "OFF") to an output line 42.

Figure 12:
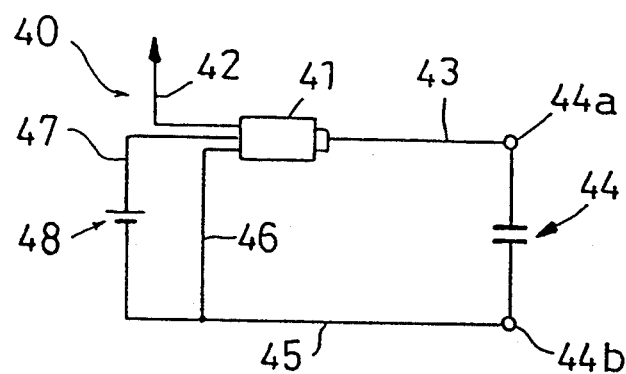
FIG. 12 is an equivalent circuit diagram of the principal portion of the third embodiment.

In a detecting circuit 40 employing this sensor 41, as shown in FIG. 12, one output line 43 of the sensor 41 is connected to one end of an equivalent capacitor 44 formed of the core 31, coating 32 and electrode 33. The other end of the capacitor 44 is connected through a ground line 45 to a negative electrode of a power source 48 and to a ground line 46 of the sensor 41. The sensor 41 receives power from the power source 48 through a source line 47. The output line 42 extends from the sensor 41 for outputting detection results.

The detecting circuit 40 operates as follows. The sensor 41, by means of the high frequency oscillator, constantly outputs a high frequency current through the output line 43. The current detector detects variations in the high frequency current due to variations in electrostatic capacity of the capacitor 44. Specifically, a high frequency current detected is compared with a predetermined threshold level and, when the high frequency current exceeds the threshold level, an "ON" state is outputted to the output line 42. If the high frequency current is below the threshold level, the output line 42 remains in "OFF" state.

Figure 11:
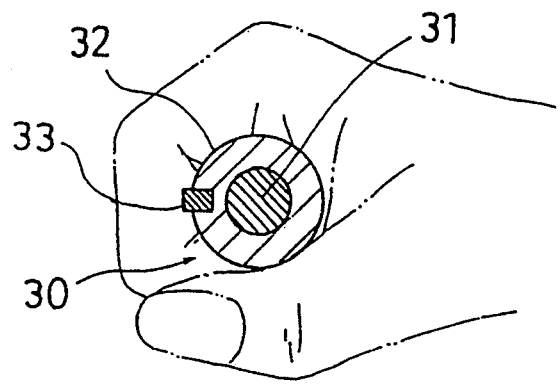
FIG. 11 is an explanatory view showing a use state of the third embodiment.

The control bar 30 has the insulating coating 32 lying between the conductive core 31 and electrode 33. Noting that this construction forms a capacitor, it may be assumed that the core 31 of the control bar 30 acts as one conductor 44a of the capacitor 44 while the electrode 33 acts as the other conductor 44b. Then, when the operator grips the control bar 30 as shown in FIG. 11, the electrostatic capacity of the capacitor 44 will be increased. Consequently, the state of the control bar 30 being gripped by the operator may be outputted to the output line 42.

Figure 13:
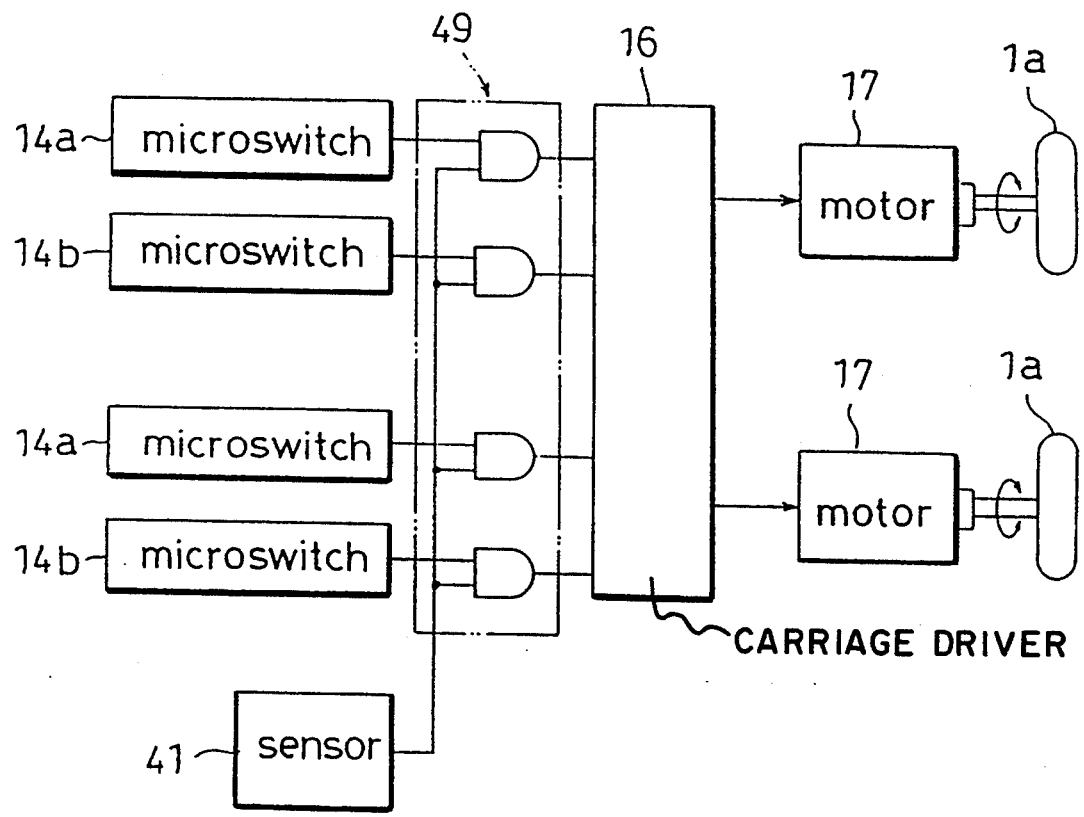
FIG. 13 is a block diagram of a control system of the third embodiment.
Figure 10:
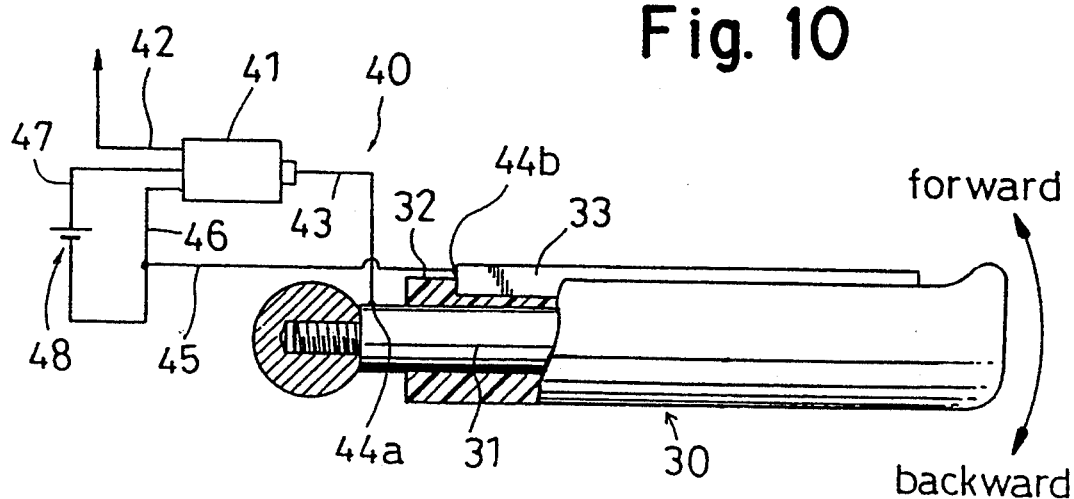
FIG. 10 is a view showing a principal portion of a third embodiment.

Based on this principle, as shown in FIG. 10, the detecting circuit 40 is formed such that the output line 43 is connected to the core 31, the electrode 33 to the ground line 46, and the output line 42 to the carriage drive unit. Then, the state of the control bar 30 being gripped by the operator may be supplied to the drive unit. The drive unit drives the drive wheel 1a only when the output line 42 is in "ON" state and the control bar 30 is pushed. Specifically, as shown in FIG. 13, detection signals of the microswitches 14a and 14b having detected displacements of a pair of control bars 30 may be applied to the carriage drive unit 16 through a group of AND circuits 49 operable by output signals of the sensor 41. In this way, the mobile X-ray apparatus is driven in an intended direction by a combination of displacements of the pair of control bars 30 gripped by the operator.

The present invention may be embodied in other specific forms without departing from the spirit or essential attributes thereof and, accordingly, reference should be made to the appended claims, rather than to the foregoing specification, as indicating the scope of the invention.

What is claimed is:

1. A mobile X-ray apparatus having a power-driven carriage with a pair of drive wheels and at least one swivelable auxiliary wheel, an X-ray tube movably supported on the carriage, and an X-ray tube control unit and a carriage drive unit mounted on the carriage, said apparatus comprising:
   a pair of control bars arranged opposite each other in a control section provided on said carriage, each of said control bars being separate from each other and supported to be independently pivotable about an axis, such that said control bars are displaceable independently from each other and substantially in a direction of movement of said carriage;
   a neutralizing mechanism for maintaining each of said control bars in a neutral position when the control bar is free from an external force;
   position detecting means for detecting displacements of said control bars in directions to drive said carriage forward and backward, respectively; and
   drive means responsive to detection signals received from said position detecting means for controlling opposite rotations of each of said drive wheels.

2. An apparatus as defined in claim 1, wherein each of said control bars is pivotable in a horizontal plane, and is disposed such that an axis thereof lies on a line extending substantially perpendicular to a direction of movement of said carriage.

3. An apparatus as defined in claim 1, wherein each of said control bars comprises an L-shaped bar having a proximal portion thereof supported to be pivotable in a vertical plane, a distal portion of each control bar being disposed such that an axis thereof lies on a line extending substantially perpendicular to a direction of movement of said carriage.

4. An apparatus as defined in claim 1, wherein said position detecting means includes microswitches for detecting the displacements of said control bars in the directions to drive said carriage forward and backward, respectively.

5. An apparatus as defined in claim 2, wherein said neutralizing mechanism includes a pair of levers each pivotably supported at one end thereof, the other ends of said levers being interconnected through a coil spring, each of said control bars being held between said levers to be maintained in the neutral position.

6. An apparatus as defined in claim 3, wherein neutralizing mechanism includes a torsion spring mounted on a pivotal axis connected to one of said control bars, said spring being engaged at one end thereof with a free end of an arm connected to said pivotal axis, and at the other end with a bracket of said pivotal axis, to maintain the control bar in the neutral position.

7. An apparatus as defined in claim 1, further comprising grip detecting means for detecting grips by an operator of said pair of control bars, said drive means validating said detection signals received from said position detecting means only when said grip detecting means outputs a detection signal.

8. An apparatus as defined in claim 7, wherein each of said control bars has an equivalent capacitor structure including a core formed of a conductive material, an insulating coating formed around said core, and a conductive element extending axially of the control bar and exposed from a periphery of said insulating coating facing the direction to drive said carriage forward, said grip detecting means being operable to detect variations in electrostatic capacity of the control bar occurring when the control bar is gripped by the operator.

* * * * *